United States Patent
Han

(10) Patent No.: US 10,471,033 B2
(45) Date of Patent: Nov. 12, 2019

(54) ORAL MICROBIOTA PROMOTION FOR IMMUNE SYSTEM ASSOCIATED INFLAMMATIONS

(71) Applicant: Knoze Jr. Corporation, Los Alamos, NM (US)

(72) Inventor: Shunsheng Han, Los Alamos, NM (US)

(73) Assignee: Knoze Jr. Corporation, Los Alamos, NM (US)

(*) Notice: Subject to any disclaimer, the term of this patent is extended or adjusted under 35 U.S.C. 154(b) by 0 days.

(21) Appl. No.: 16/001,808

(22) Filed: Jun. 6, 2018

(65) Prior Publication Data
US 2019/0083435 A1     Mar. 21, 2019

Related U.S. Application Data

(63) Continuation-in-part of application No. 15/706,323, filed on Sep. 15, 2017.

(51) Int. Cl.

| | | |
|---|---|---|
| A61K 31/198 | (2006.01) | |
| A61K 9/00 | (2006.01) | |
| A61K 35/744 | (2015.01) | |
| A61K 31/7004 | (2006.01) | |
| A61K 31/733 | (2006.01) | |
| A61K 31/719 | (2006.01) | |
| A61K 31/047 | (2006.01) | |
| A61K 38/46 | (2006.01) | |
| A61K 38/48 | (2006.01) | |
| A61C 19/06 | (2006.01) | |
| A23L 33/175 | (2016.01) | |
| A23L 33/125 | (2016.01) | |
| A23L 33/135 | (2016.01) | |
| A61K 38/51 | (2006.01) | |
| A61K 36/725 | (2006.01) | |
| A61F 7/00 | (2006.01) | |
| A61K 35/00 | (2006.01) | |

(52) U.S. Cl.
CPC .......... *A61K 31/198* (2013.01); *A23L 33/125* (2016.08); *A23L 33/135* (2016.08); *A23L 33/175* (2016.08); *A61C 19/063* (2013.01); *A61K 9/0056* (2013.01); *A61K 31/047* (2013.01); *A61K 31/7004* (2013.01); *A61K 31/719* (2013.01); *A61K 31/733* (2013.01); *A61K 35/744* (2013.01); *A61K 36/725* (2013.01); *A61K 38/465* (2013.01); *A61K 38/4886* (2013.01); *A61K 38/51* (2013.01); *C12Y 301/21* (2013.01); *C12Y 304/24057* (2013.01); *C12Y 402/02* (2013.01); *A23V 2002/00* (2013.01); *A61F 7/00* (2013.01); *A61F 2007/0017* (2013.01); *A61F 2007/0059* (2013.01); *A61K 2035/115* (2013.01)

(58) Field of Classification Search
CPC ............ A61K 2035/115; A61K 35/744; A61K 9/0056; A61C 19/063
See application file for complete search history.

(56) References Cited

U.S. PATENT DOCUMENTS

| | | | | |
|---|---|---|---|---|
| 5,468,777 A | * | 11/1995 | France ................... | A61K 8/447 424/49 |
| 5,558,071 A | * | 9/1996 | Ward ....................... | F02P 3/02 123/598 |
| 6,579,851 B2 | * | 6/2003 | Goeke .................... | A61K 38/26 514/11.7 |
| 8,461,129 B2 | * | 6/2013 | Bolduc ................... | A61L 15/28 127/49 |
| 2011/0028412 A1 | * | 2/2011 | Cappello ............ | A61K 31/7004 514/25 |
| 2013/0041004 A1 | * | 2/2013 | Drager ..................... | A61K 9/08 514/394 |
| 2013/0084243 A1 | * | 4/2013 | Goetsch ............. | C07K 16/2863 424/1.49 |
| 2013/0096073 A1 | * | 4/2013 | Sidelman ........... | A61K 38/1709 514/21.6 |
| 2016/0324766 A1 | | 11/2016 | Stettler et al. | |
| 2017/0071986 A1 | * | 3/2017 | Kovarik ............ | A61K 39/0007 |

OTHER PUBLICATIONS

Breadsmith (https://www.breadsmith.com/product/cranberry-sourdough-whole-grain/) available Apr. 5, 2016, pp. 1-3 (Year: 2016).*
Tea Blog (https://beleaveteas.com/blog/three-delectable-teas-to-pair-with-your-thanksgiving-dinner-and-make-it-unforgettable/) available Jul. 11, 2015, pp. 1-5 (Year: 2015).*
Livestrong arginine (https://www.livestrong.com/article/275892-foods-high-in-l-arginine/) Feb. 4, 2019, pp. 1-5 (Year: 2019).*
Tenjo, E. et al. "Salivary deoxyribounuclease I polymorphism separated by polyacrylamide gel-isoelectric focusing and detected by the dried agarose film overlay method" Electrophoresis 1993, 14, 1042-1044 (Year: 1993).*
Newman et al. "The effect of hot beverages, cold beverages, and chewing gum on oral temperature" Transfusion 2001, 41, 1241-1243 (Year: 2001).*

(Continued)

*Primary Examiner* — Andrew S Rosenthal
(74) *Attorney, Agent, or Firm* — James C. Kennedy III Esq., LLC; James C. Kennedy, III

(57) ABSTRACT

A method of promoting a desired oral microbiota to treat an inflammation condition related to an allergic reaction in a subject in need of such treatment including providing a preformulated edible composition including an amino acid containing ingredient comprising L-arginine, the composition configured to be present as individual molecules of L-arginine within an oral cavity of the subject; removing a biofilm from surfaces within an oral cavity including exposing the biofilm to a biofilm degrading enzyme; wherein during or following removal of the biofilm, the composition is provided contained and at least partially dissolved within an oral cavity of the subject for a period of at least from about 30 seconds to about an hour on a daily basis comprising at least one day to promote an increased concentration of selected oral microbiota, the selected microbiota including *Veillonella* and *Streptococcus*.

25 Claims, No Drawings

(56) References Cited

OTHER PUBLICATIONS

Livestrong (https://www.livestrong.com/article/165530-foods-containing-protease/) available Jul. 26, 2010, pp. 1-3 (Year: 2010).*
Chen, H. et al. "Screening of carbon sources/prebiotics and amino acids in the medium for *Streptococcus thermophilus* using Plackett—Burman design" Journal of Chemical and Pharmaceutical Research, 2013, 5(12):975-980 (Year: 2013).*
Tea Blog (https://beleaveteas.conn/blog/three-delectable-teas-to-pair-with-your-thanksgiving-dinner-and-nnake-it-unforgettable/) available Jul. 11, 2015, pp. 1-5 (Year: 2015).*
Kolderman et al. "L-Arginine Destabilizes Oral Multi-Species Biofilm Communities Developed in Human Saliva" (PLoS One 2015, 10(5): e0121835, pp. 1-18) (Year: 2015).*
Breadsmith (https://www.breadsmith.com/product/cranberry-sourdough-whole-grain/) available Apr. 5, 2016, p. 1-3 (Year: 2016).*
Koopman et al. "Changes in the oral ecosystem induced by the use of 8% arginine toothpaste" (Archives of Oral Biology 73 (2017) 79-87) (Year: 2017).*
MyFood Data (https://tools.myfooddata.com/protein-calculator.php?foods=05220-05220-05220&serv=wt1-wt1-wt1&qty=1-1-1) accessed Dec. 4, 2018, pp. 1-2 (Year: 2018).*
Livestrong arginine (https://www.livestrong.conn/article/275892-foods-high-in-l-arginine/) Feb. 4, 2019, pp. 1-5 (Year: 2019).*
David P. Strachan, Hay fever, hygiene, and household size, Br. Med. j. 1989;299:1259-60, BMJ, United Kingdom.
H. Odkada, C. Kuhn, H. Feillet, and J.F.Bach,The 'hygiene hypothesis' for autoimmune and allergic diseases: an update, Clinical and Experimental Immunology, 2010:160:1-9, British Society for Immunology, United Kingdom, Wiley.
Samuel J. Arbes, Jr. et. al.,Can oral pathogens influence allergic disease?, May 2011,vol. 127, Issue 5, pp. 1119-1127, American Academy of Allergy, Asthma & Immunology, Elsevier Inc.,US.
Cliff Shunsheng Han, A specific hygiene hypothesis, Medical Hypotheses 93 (2016) 146-149, Elsevier Inc., US.
A. Tedeschi et. al., Clinical Exp. Allergy., 2003, 33:449, 454, Blackwell publishing, Oxford, England.
Caelos A. Cuello-Garcia et.al., Probiotics for the prevention of allergy: A systematic review and meta-analysis of randomized controlled trials, Oct. 2015 vol. 136, Issue 4, pp. 952-961,American Academy of Allergy, Asthma & Immunology, Elsevier Inc., US.
Hosana G. Rodrigues et. al., Fattyacids as modulators of neutrophil recruitment, function and survival, European Journal of Pharmacology 785(2016) 50-58, Elsevier Inc.,US.
Renan Oliveira Corrêa et. al., Regulation of immune cell function by short-chain fatty acids, Clinical & Translational Immunology (2016) 5, e73; doi:10.1038/cti.2016.17 & 2016 Australasian Society for Immunology Inc., Campinas, São Paulo, Brazil.
Ken Kikuchi et al., Comparison of Phenotypic Characteristics, DNA-DNA Hybridization Results, and Results with a Commercial Rapid Biochemical and Enzymatic Reaction System for Identification of Viridans Group Streptococci, Journal of Clinical Microbiology, May 1995, p. 1215-1222, American Society for Microbiology, US.
Alan L. Coykendall, Classification and Identification of the Viridans Streptococci, Clinical Microbiology Reviews, Jul. 1989, p. 315-328, American Society for Microbiology, US.
Jessica E. Koopman et al. ,Stability and Resilience of Oral Microcosms Toward Acidification and Candida Outgrowth by Arginine Supplementation, Microb Ecol (2015) 69:422-433, Springer Science+Business Media New York 2014.
J.A. Durant et al., Comparison of Batch Culture Growth and Fermentation of a Poultry Veillonella Isolate and Selected Veillonella Species Grown in a Defined Medium ,Anaerobe (1997) 3, 391-397,1997 Academic Press, US.
Jessica E. Koopman et al., Changes in the oral ecosystem induced by the use of 8% arginine toothpaste, Archives of Oral Biology 73 (2017) 79-87, 2016 Elsevier Ltd, US.
Ethan Kolderman et al., L-Arginine Destabilizes Oral Multi-Species Biofilm Communities Developed in Human Saliva, PLOS ONE | DOI:10.1371/journal.pone.0121835 May 6, 2015.

* cited by examiner

ORAL MICROBIOTA PROMOTION FOR IMMUNE SYSTEM ASSOCIATED INFLAMMATIONS

The disclosure generally relates to compositions and methods for treating immune system modulated Inflammations including methods for partial or substantial removal of biofilms, including oral biofilms to aid in the selective altering of bacterial populations in a microbiome to promote healthy operation of the immune system.

More particularly, the disclosure relates to compositions and methods for treating Immune System modulated Inflammations including partial or substantial removal of biofilms that may have the advantageous effect of aiding in the targeted modulation of bacteria populations including the oral microbiota. The selected altering of the oral microbiota may thereby promote the naturally occurring healthy operation of the immune system including reducing respiratory allergic reactions (including allergic reactions to self-antigens that lead to autoimmune diseases) as well as other oral and/or sinus infections and/or inflammations.

BACKGROUND

In general, the prevalence of allergic diseases has dramatically increased in recent decades and currently affects more than sixty million people in the United States, reducing the quality of life. It is believed and has been found that the presence of certain oral bacteria species/strains may affect the aggressiveness of response of the immune system including with respect to allergic reactions as well as contributing to other oral and/or sinus infections. More specifically, while not intending to be bound by any health claims, it is believed that the reduction of normally occurring (commensal) oral bacteria in the normally occurring oral microbiota, for example, by aggressive dental hygiene practices, may serve to make non-pathogenic antigens, such as pollen, more prevalent and visible to the immune system. It is further believed, that as a result, non-pathogenic antigens may be more readily targeted by the immune system, leading to exacerbated allergic reactions and/or inflammations (including allergic reactions to self-antigens that lead to autoimmune diseases) as well as other oral and/or breathing passage associated infections and/or inflammations.

For example, oral hygiene hypothesis (OHH) is one aspect of a more general hygiene hypothesis (HH), which was proposed more than two decades ago (see Strachan, D. P. "Hay fever, hygiene, and household size", British Medical Journal 299, 1259-1260 (1989)) to explain the rise in allergic diseases. Numerous scientific studies have since provided support for HH, generally showing a relation between increased exhibition of allergies in association with modern social practices, such as formula infant feeding, antibiotic use, urban living, and reduction in family size (see e.g., Okada, H., Kuhn, C., Feillet, H. & Bach, J. F., "The hygiene hypothesis for autoimmune and allergic diseases: an update" Clin. Exp. Immunol. 160, 1-9 (2010)). Although the molecular mechanisms of immune system modulation by gut microbiota are well understood, efforts to reduce allergic reactions through microbial intervention, such as by the use of probiotics have shown inconsistent results.

Extensive oral hygiene practices, according to oral hygiene hypothesis (Han, C S., "A specific hygiene hypothesis" Med. Hypotheses 2016 August; 93:146-149), are believed to cause the exacerbation of naturally occurring respiratory allergies, such as allergic rhinitis (AR), one of the most common allergic conditions.

Conversely, again not intending to be bound by theory and health claims, it is believed that an over-abundance of certain normally occurring (commensal) oral bacteria in the normally occurring oral microbiota, for example, caused by a de-sensitized or abnormally functioning immune system may cause normally non-pathogenic normally occurring oral bacteria to become pathogenic, resulting in chronic attack and resulting inflammation by the immune system thereby resulting in chronic pathogenic conditions related to several types of oral and/or breathing passage related inflammations, infections and/or obstructions associated with exacerbated allergic reactions and/or inflammations (including allergic reactions to self-antigens that lead to autoimmune diseases).

There is therefore a need for an oral microbiota promoting composition that selectively promotes a desired oral microbiota and method of using the same that has the effect of promoting the healthy operation of the immune system and which may have the functional effect of promoting an improved response to allergens as well as reducing associated allergic reactions and/or inflammations (including allergic reactions to self-antigens that lead to autoimmune diseases) as well as other oral and/or breathing passage associated infections and/or inflammations.

It is an object of the invention to provide an oral microbiota promoting composition that selectively promotes a desired oral microbiota and method of using the same that has the effect of promoting the healthy operation of the immune system and which may have the functional effect of promoting an improved response to allergens as well as reducing associated allergic reactions and/or inflammations (including allergic reactions to self-antigens that lead to autoimmune diseases) as well as other oral and/or breathing passage associated infections and/or inflammations.

SUMMARY

A method of promoting a desired oral microbiota to treat an inflammation condition related to an allergic reaction in a subject in need of such treatment including providing a preformulated edible composition including an amino acid containing ingredient comprising L-arginine, the composition configured to be present as individual molecules of L-arginine within an oral cavity of the subject; removing a biofilm from surfaces within an oral cavity including exposing the biofilm to a biofilm degrading enzyme; wherein during or following removal of the biofilm, the composition is provided contained and at least partially dissolved within an oral cavity of the subject for a period of at least from about 30 seconds to about an hour on a daily basis comprising at least one day to promote an increased concentration of selected oral microbiota, the selected microbiota including *Veillonella* and *Streptococcus*.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

It is believed, and has been found that according to the oral hygiene hypothesis (OHH) noted above, that persistent and intensive hygiene practices, together with other life events, such as fever and/or antibiotic usage, will likely change the oral microbiota of an individual. The oral cavity is a complex environment with many different surfaces as biological niches, such as the tongue, gums, teeth and other oral cavity surfaces. Normally occurring microbiota associated with these niches are different and are believed to have a different effect on normal functioning of the immune system.

Likewise, it is believed, and has been unexpectedly found, that the introduction of selected microbiota-promoting substances into the oral cavity in a controlled manner may either promote or decrease the populations of naturally occurring oral bacteria species/strains. The decrease of targeted naturally occurring bacteria may be accomplished by promoting competing bacteria or by exposing the targeted bacteria to a substance which decreases the targeted bacteria population. Selective Control of the relative populations of selected bacteria populations may in turn have an associated effect of modulating or reducing the intensity of oral and/or sinus inflammations, and/or allergic reactions, and/or pulmonary inflammations.

While not intending to be bound by any particular theory of operation, and making no specific health claims, it is believed that oral microbiota interact with the host largely through metabolites produced by its relevant bacterial members. Those metabolites, such as but not limited to short chain fatty acid, may influence the function of multiple biologic systems and organs, such as the immune system. Missing or severe reduction of the relevant naturally occurring beneficial (commensal) bacteria may cause malfunctioning of the immune system, such as causing over-sensitivity to commensal bacteria and/or allergens (including self-antigens). Commensal microflora (normal microflora, indigenous microbiota) consists of those micro-organisms, which are present on body surfaces covered by epithelial cells and are exposed to the external environment (gastrointestinal and respiratory tract, vagina, skin, etc.).

It is known that in both autoimmune and inflammatory diseases, the condition arises through aberrant responses of the human immune system to antigens including self-antigens (originating from within the body). In autoimmunity, the patient's immune system is activated against the body's own proteins by a response to self-antigens.

Under specific conditions, the commensal bacteria may become opportunistic pathogens and may overcome protective host responses and exert pathologic effects. Therefore, in one embodiment it is believed that the immune system response to the allergens (including self-antigens) and/or commensal bacteria may be modulated by the method and/or composition such that the associated oral and/or breathing passage inflammations and/or allergic reaction symptoms are suppressed relative to what an infection and/or allergic reaction may be with an unhealthy level of, or different commensal microbiota. It is further believed and evidence suggests that over time, as a result of promoting a healthy oral microbiota with selected microbiota-promoting substances that the immune system may function in a healthy manner with a health promoting response to allergens, (including self-antigens), and/or commensal bacteria that have become pathogenic.

Furthermore, due to the connectivity among mouth and respiratory duct and lungs, a healthy oral microbiota may lead to a healthy microbiota in the lungs as well. Eventually the method and/or composition may benefit the healthy functioning of the immune system which may in turn have a healthy response not only to oral and/or breathing passage inflammations related to an allergic response but also relevant inflammations in the lungs, such as asthma or pulmonary obstructions.

For example, in other embodiments, the method and/or composition may benefit the healthy functioning of an over-sensitized or under-sensitized immune system with respect to oral and/or sinus inflammations or infections including breathing passage related inflammations including but not limited to inflammations related to gingivitis, periodontitis (periodontal disease), tonsillitis, rhinosinusitis, pharyngitis, laryngitis, and pulmonary obstructions. While some or a portion of these inflammations may be caused by pathogen invasion, an overly sensitized immune system attacking commensal bacteria may lead to the exacerbation and/or cause of inflammations associated with other opportunistic (pathenogenic) commensal bacteria caused infections.

In other embodiments, the method and/or composition may benefit the healthy functioning of an over-sensitized or under-sensitized immune system with respect to inflammatory conditions associated with autoimmune diseases including autoimmune reactions locally in the neck/head area or in other parts of the body, such as but not limited to alopecia, arthritis, systemic lupus and erythematosus.

In an under-sensitized immune system some or a portion of these inflammations may be caused by commensal bacteria becoming pathogenic (opportunistic) resulting in chronic attack by the immune system leading to the exacerbation and/or cause of inflammations including those associated with oral cavity and/or breathing passage related inflammations.

The method and/or composition may be used to promote a healthy functioning of an immune system e.g., by reducing immune system sensitivity in an over-sensitized immune system or increasing immune system sensitivity in an under-sensitized immune system by restoring a healthy level of desired commensal bacteria to thereby at least reduce or alleviate symptoms associated with immune system promoting inflammatory conditions including oral and/or breathing passage related inflammations, infections, obstructions, and/or allergens.

In one embodiment, an oral microbiota promoting composition may be provided into an oral cavity that may have the effect of promoting desired microbiota within an oral cavity.

In another embodiment, a method of applying an oral microbiota promoting composition (prebiotic) may be provided that may have the effect of promoting desired microbiota within an oral cavity and have the desired functional effect of treating oral cavity and/or sinus inflammations including breathing passage inflammations and/or obstructions related to allergic reactions.

In one embodiment, promoting desired microbiota within an oral cavity may be accomplished by promoting an increase in the relative concentration of selected bacterial species. For example the desired selected bacterial species may be increased to a relative concentration (relative to all other types of bacterial species percent within the oral cavity) of from about 5% to about 30%, more preferably, from about 6% to about 20%, even more preferably from about 8% to about 12% of the relative types of bacterial present within the oral cavity.

In some embodiments, the relative percentage of the desired bacterial species population within the oral cavity may be determined by one or more of weight, volume, and/or individual bacterium counting methods and be primarily with respect to substantially similar comparative samples taken from one or more of saliva, tongue, throat, and inside surfaces of the oral cavity including dental portions.

In another embodiment, promoting desired microbiota within an oral cavity may be accomplished by promoting a decrease in the relative concentration of selected bacterial species. For example the desired selected bacterial species may be decreased to a relative concentration (relative to all types of bacterial species present) of from about 5% to about 30%, more preferably, from about 6% to about 20%, even more preferably from about 8% to about 12%.

In one embodiment, promoting desired microbiota within an oral cavity may be accomplished by exposing the microbiota within an oral cavity to a substance that promotes the growth of targeted (selected) bacteria that comprises the desired microbiota.

In another embodiment, promoting desired microbiota within an oral cavity may be accomplished by exposing the microbiota within an oral cavity to a substance that inhibits in some degree, the growth of targeted bacteria that comprises the desired microbiota.

In one embodiment, the targeted bacterial species may comprise one or more desired microbial members such as *Veillonella* including associated species, such as, but not limited to, *Veillonella* species such as (V.) *dispar* and (V.) *parvula* and *Streptococcus* species including one or more associated species, such as, but not limited to, (S.) *salivarius* (S.) *australis, S. gordonii* and (S.) *thermophilus*.

In another embodiment, the targeted bacterial species may comprise a species other than the one or more desired microbial members that may have the effect of crowding out or replacing the population of beneficial bacterial species and thereby reducing the relative concentration (relative with respect to a selected one and/or all other bacterial species present) of untargeted bacterial populations that have reached an undesireably high relative concentration.

For example in one embodiment if it is determined that one or more of the desired bacterial species including *Veillonella* species such as (V.) *dispar* and (V.) *parvula*, and *Streptococcus* species such as (S.) *australis, S. gordonii* and *S. salivarius* have reached an undesirably high concentration e.g., from about 70 percent to about 100 percent (with respect to all bacterial species present), then a competing bacterial species, such as *S. mitis* and *S. dentisani*, and the like, may be selectively promoted in order to compete with and thereby reduce (crowd out) concentrations of the overly-concentrated bacterial populations For example, in one embodiment, competing bacterial species may be promoted by changing the composition of an oral microbiota promoting composition, e.g., an oral microbiota promoting composition that has the effect of promoting desired *Veillonella* and/or *Streptococcus* species may be made less promoting to the desired bacterial species and/or more promoting to a competing bacterial species by leaving out one or more ingredients, such as one or more sugars, adding alternative ingredients such as raffinose, which is preferred by *S mitis*.

Alternatively or additionally, an undesirably high population of normally beneficial species such as *Veillonella* or *Streptococcus* may be reduced and re-established at a lower relative concentration level (relative to a selected one or more bacterial populations present in the oral cavity) or by removing a biofilm within the oral cavity and applying an oral microbiota promoting composition as outlined below. For example, partially or substantially removing a biofilm within the oral cavity and/or applying the oral microbiota promoting composition may have the beneficial effect of resetting or adjusting selected oral microbiota concentrations including desired relative concentrations of the desired bacterial species such as *Veillonella* and/or *Streptococcus* as previously discussed.

For example, in one embodiment, the relative desired level of desired bacterial species may be from about 30 percent to about 80 percent (e.g., based on a counting percentage of a selected bacterial species with respect to all bacterial species present in the oral cavity), more preferably from about 40 percent to about 70 percent, even more preferably from about 50 percent to about 60 percent.

In one embodiment, a method of applying an oral microbiota promoting composition may include multiple instances of introduction of the composition into the oral cavity (mouth) in the form of a solid, powder, paste, or liquid in the amount of about 1 gm to about 500 gms at one time or multiple times in fractional amounts. Where the oral microbiota promoting composition is in the form of liquid, the method may include dissolving the composition in a liquid In another embodiment, a method of applying an oral microbiota promoting composition may include swallowing the composition following introduction of the composition into the oral cavity and following a period of retaining the composition within the mouth for a select period of time including e.g., chewing, gargling, and/or sublimating (dissolving) the composition while within the oral cavity.

In another embodiment, a method of applying an oral microbiota promoting composition may include removing the composition following introduction into the oral cavity by expelling (e.g., pulling out or spitting-out) the microbiota promoting composition following a period of retaining the composition within the mouth.

In another embodiment, a method of applying an oral microbiota promoting composition may include retaining the microbiota promoting composition within the oral cavity from about 10 seconds to about an hour, more preferably, from about 5 minutes to about 30 minutes on a daily basis for a period of about 2 days to about 60 days.

In another embodiment, a method of applying an oral microbiota promoting composition may include introducing the microbiota promoting composition for relatively short periods several times a day, for example from about 1 second to about 30 seconds, each from about 3 to about 10 times a day for a period of about 2 days to about 60 days.

In another embodiment, a method of applying an oral microbiota promoting composition may include extending the periods of introduction of the microbiota promoting composition into the oral cavity, for example, from about every 3 days to about every 10 days, including stopping the introduction of the composition following the disappearance of allergy symptoms.

In another embodiment, a method of applying an oral microbiota promoting composition may include at least partially, more preferably substantially, removing a mucosal film (biofilm) from surfaces within the oral cavity prior to or while administering the microbiota promoting composition to the oral cavity. By the term substantially removed is meant removal of from about 70% to about 100% of a biofilm as determined by sampling saliva and/or surfaces defining major surface areas (e.g. samples from one or more of the tongue, mouth, throat, and teeth) within the oral cavity, e.g., removing from about 70% to about 100% of a biofilm from greater than about 90% of the sampled surface areas supporting the biofilm within the oral cavity.

Biofilms are defined as living bacterial populations adherent to each other and/or to surfaces including within porous surfaces and which populations live within a matrix of cells and extracellular polymers including those produced by the bacterial populations. A biofilm possesses a natural resistance to surfactants and other chemicals and provides protection from antibacterial agents which may be effective against free-floating or planktonic bacteria outside the biofilm.

In one embodiment, a biofilm with the oral cavity may be substantially removed by exposing the biofilm to one or more biofilm degrading enzymes that may be effective in disrupting the matrix of extracellular polymers. By disrupting is meant chemically changing the matrix of extracellular polymers sufficient to allow chemical penetration of the matrix by the one or more enzymes and/or other chemicals or antibacterial agents.

It is well known in the art that the matrix of extracellular polymers includes polysaccharides (exopolysaccharides) that function as a backbone of the biofilm and include one or more of glucose, galactose, mannose, fructose, rhamnose, ribose, glucosamine, galactosamine, mannuronic acid, galacturonic acid and glucuronic acid (see I. W. Sutherland in "Surface Carbohydrates of the Procaryotic Cell", 27-96, Academic Press, London, 1977, which is hereby incorporated by reference).

In one embodiment, the one or more biofilm degrading enzymes may include deglycosylate biopolymers such as glycoproteins. For example, the enzyme may include one or more endoglycosidases.

It will be appreciated that known methods including methods using r-DNA together with selected bacterial strains to produce and isolate enzymes are known in the art and may be used to produce the one or more biofilm degrading enzymes.

In another embodiment the one or more biofilm degrading enzymes may be included in a mixture of enzymes including one or more of alpha-amylase, a protease and a cellulase (see U.S. Pat. No. 5,071,765, which is hereby incorporated by reference).

In another embodiment, the one or more biofilm degrading enzymes may be included in a mixture of enzymes including one or more of galactosidase, galacturonidase, rhamnosidase, xylosidase, fucosidase, arabinosidase and alpha-glucosidase (see U.S. Pat. No. 5,238,572, which is hereby incorporated by reference).

In another embodiment the one or more biofilm degrading enzymes may be included in a mixture of enzymes including one or more of polysaccharidases, proteases, lipases and glycoproteases (see EP0820516B1, which is hereby incorporated by reference).

In another embodiment the one or more biofilm degrading enzymes may be include glycosidases.

In another embodiment the one or more biofilm degrading enzymes may include DNase I of bacterial origin or DNase enzymes isolated from other organisms including humans (see US Patent US20130052250A1 which is incorporated herein by reference) US20130052250A1.

In another embodiment the one or more biofilm degrading enzymes may be include polysaccharide hydrolases such as Glucan hydrolases including one or more of mutanases and dextranases (see Pleszczyńska, M. Wiater, A. Bachanek, T. Szczodrak J., "Enzymatic removal and disinfection of bacterial biofilms", Biotechnology and Applied Biochemistry, 2017, which is hereby incorporated by reference).

In one embodiment the one or more biofilm degrading enzymes may include a polysaccharide-degrading enzyme.

In another embodiment the one or more biofilm degrading enzymes may include one or more hydrolytic enzymes capable of degrading an exopolysaccharide backbone structure of a biofilm which may include alginates formed by bacteria within the biofilm (see U.S. Pat. No. 6,830,745B1, which is hereby incorporated by reference).

In another embodiment the one or more biofilm degrading enzymes may include one or more hydrolytic enzymes capable of degrading proteins, polypeptides, and lipids, such as lipopolysaccharides and lipoproteins comprising the biofilm.

In another embodiment, the one or more biofilm degrading enzymes may include one or more chemical moieties attached to the one or more enzymes that have the capability of binding to the biofilm, e.g., either through hydrogen bonding such as with amine or carboxylate containing moieties or covalently such as through nitrogen-nitrogen, nitrogen-carbon or carbon-carbon bonding.

In another embodiment, the one or more biofilm degrading enzymes may include a functional ability to generate an active oxygen species including oxido-reductases.

In another embodiment, the one or more biofilm degrading enzymes may include polysaccharide lyases.

In one embodiment, the one or more biofilm degrading enzymes may include lyases capable of lysing alginate, such as alginates forming a portion of the biofilm (see EP0642795B1, which is hereby incorporated by reference).

In another embodiment, non-enzymatic bactericidal components such as antimicrobial agents, antibiotics, and sanitizing agents may be provided with or separately from the one or more enzymes.

For example, the one or more biofilm degrading enzymes and/or non-enzymatic bactericidal components may be provided into the oral cavity by a carrier including a solid or liquid carrier such as a solution, spray, tablet, or emulsion, and/or released into the oral cavity by being provided in a carrier or supported on a bio-adhesive support using similar methods further discussed below for delivering a preferred microbiota promoting composition. In some embodiments the biofilm degrading enzymes may be delivered with or separately from the preferred microbiota promoting composition.

In one embodiment the biofilm may be at least partially removed, including substantially removed (e.g., from about 70% to near 100% (e.g., by weight, volume, bacterium counting, and/or surface area of the biofilm) or more preferably, greater than about 95%), by raising the whole body temperature, or at least the oral cavity temperature to a temperature from about from about 90 to about 130 degrees Fahrenheit for a short time period, e.g., from about 1 minute to about 1 hour, for example, with conventional biological or physical means.

In another embodiment, the biofilm may be substantially removed by exposing the biofilm to one or more biofilm degrading enzymes together with substantially simultaneously or sequentially raising the temperature within the oral cavity. The combination of methods may be performed substantially simultaneously or sequentially in any order.

In one embodiment, the one or more biofilm degrading enzymes may be provided within the oral cavity to initially disrupt the biofilm, followed by heating the oral cavity.

In another embodiment, the oral cavity may be first heated, followed by the use of the one or more biofilm degrading enzymes, including optionally heating the oral cavity subsequent to the use of the one or more enzymes.

In another embodiment, rubbing or scrubbing the inside of the oral cavity may be performed substantially simultaneously or sequentially to steps including one or more of heating and/or using one or more biofilm degrading enzymes to at least partially, including substantially, removing the biofilm.

For example, the use of one or more biofilm degrading enzymes may be provided prior to or substantially simultaneously with rubbing and/or brushing the inside of the oral cavity, followed by heating the inside of the oral cavity with a heated liquid with optional additional rubbing and/or brushing to at least partially and/or substantially removing the biofilm.

It will be appreciated that the rubbing or brushing may be performed by any conventional method including with one or more of a brush, such as a toothbrush, a scrapper and/or a wet cloth, which may optionally include the prior, simultaneous or subsequent use of sonic energy applied to the rubbed or brushed area of the oral cavity.

In a related embodiment, the biofilm may be at least partially and/or substantially removed where heating the inside of the oral cavity may be include rinsing of the oral cavity (mouth) with a heated liquid, such as a water-containing liquid (optionally including prior, simultaneous, and/or subsequent brushing or rubbing).

In some embodiment, the temperature of the heated liquid may be from about 80 to about 130 degrees Fahrenheit, more preferably from about 90 to about 120 degrees Fahrenheit, even more preferably from about 100 to about 110 degrees Fahrenheit.

In some embodiments, the oral rinsing may include periodic rinsing, for example, multiple periods where each period is preformed for about 10 seconds to about 30 seconds over a period of from about 5 to about 15 minutes.

In some embodiments the removal of the biofilm within the oral cavity may take place prior to and/or substantially simultaneous with the application of a microbiota promoting composition within the oral cavity.

It will be appreciated that at least partially removing, including substantially removing a biofilm from surfaces within the oral cavity, for example, biofilms on the dental surfaces and tongue, has been found to improve the operation of promoting desired selected bacteria to achieve a desired oral microbiome by the use of the oral microbiota promoting composition.

In another embodiment, the oral microbiota promoting composition may be formulated into oral dosage forms such as tablets, caplets, and capsules, or a powder formulation or that may be dissolved in a liquid, for example diluted in a liquid having a ratio of from about 1:1 to about 1:500 with respect to either weight or volume of the liquid (e.g., the liquid being larger number).

In another embodiment, the oral microbiota promoting composition may be formulated or manufactured as a chewing gum or candy, or other edible carrier, for example as an additive having a ratio of from about 1:1 to about 1:500 with respect to either weight or volume of the edible carrier (e.g., larger number).

In another embodiment, the oral microbiota promoting composition may be formulated as an additive to an oral hygiene product acting as a carrier, such as toothpaste or mouthwash, the microbiota promoting composition having a ratio of from about 1:1 to about 1:500 with respect to either weight or volume of the oral hygiene product.

In another embodiment, the oral microbiota promoting composition may be provided on bioadhesive delivery devices such as bioadhesive strips that are known in the art. For example, the composition may be provided on or infused into a bioadhesive strip, such as on a bioadhesive or self-adhesive support which supports the composition. For example, the composition may be included in a gel, such as a carbohydrate based gel that may be supported on a solid support, such as a plastic or cross-linked polymer support that may include micro-patterns on a supporting surface (e.g., having spacings of about 0.1 to about 2 mm). The bioadhesive strip infused with or supporting the oral microbiota promoting composition may be self-adhesive (in the presence of oral saliva) to dental or mucosal portions of the oral cavity.

In a related embodiment, the one or more enzymes may be provided within the bioadhesive delivery device, and formulated to be released into the oral cavity prior to and/or substantially simultaneous with the release of the oral microbiota promoting composition. For example, the one or more enzymes and the oral microbiota promoting composition may be formulated for controlled time-release for example by mixing with or encapsulating within time-release dissolving substances that are known in the art.

In another embodiment, in a method of manufacturing an oral microbiota promoting composition may be formulated having an edible foodstuff as a carrier, the microbiota promoting composition having a ratio of from about 1:1 to about 1:500 with respect to either weight or volume of the edible foodstuff.

In one embodiment, the desired microbial species/strains promoted in the oral cavity by the oral microbiota promoting composition may be naturally occurring within the oral cavity and/or may be provided separately or within the oral microbiota promoting composition.

In a related embodiment, the desired microbial species/strains may be present in the oral cavity or in the oral microbiota promoting composition at a level of from about 1000 to about 1,000,000,000 living cells.

It will be appreciated that the desired microbial species/strains may be naturally occurring and/or may be obtained commercially and handled in accordance with any applicable safety requirements.

In another embodiment, the desired microbial species/strains promoted in the oral cavity by the oral microbiota promoting composition may include at least a first microbial species that can attach to surfaces (e.g., teeth, tongue, mouth) within the oral cavity and at least one second microbial species that may attach to the same or different surfaces and/or may attach to the at least first microbial species.

In a related embodiment, the at least a first and second microbial species may produce a product, such as a sugar containing moiety, that may be metabolized by the other of the at least a first and second microbial species.

In one embodiment, one of the desired microbial members promoted within the oral cavity promoted by the oral microbiota promoting composition may include one or more live bacterium with lactate fermenting capability such as, but not limited to *Veillonella*, which further may include one or more of associated species, such as, but not limited to, *Veillonella* (*V.*) *dispar* and *Veillonella* (*V.*) *parvula*.

In one embodiment, one of the desired microbial species/strains promoted within the oral cavity promoted by the oral microbiota promoting composition may include one or more live lactic acid producing bacterium such as but not limited to *Streptococcus* including one or more of associated species, such as, but not limited to, *Streptococcus (S.) salivarius* and *Streptococcus (S.) thermophilus*.

In a related embodiment, the desired microbial species/strains promoted within the oral cavity by the oral microbiota promoting composition may include at least one live lactic acid producing bacterium and at least one live lactate fermenting bacterium such as, but not limited to, respectively, *Veillonella* and *Streptococcus* and their respectively associated preferred species stated above.

In another embodiment, an oral microbiota promoting composition is provided that includes at least one amino acid or amino acid containing substance including at least L-arginine. The at least one amino acid may further or alternately include at least one of L-cysteine, DL-aspartic acid, L-glutamic acid, L-serine and L-tyrosine including phosphates, salts, acids, and enzymes comprising the same.

In preferred embodiments, the at least one amino acid may be introduced into the composition including substantially (e.g., greater than about 90%) individual molecules (as opposed to amino acid chains) of a respective amino acid, or at least individual molecules of the amino acid L-arginine. In another embodiment, the at least one amino acid may be substantially decomposed into individual molecules of the amino acid following introduction into the oral cavity. In another embodiment, the amino acid L-arginine, is configured to be present substantially as individual molecules with the oral cavity, e.g., dissolve and/or decompose and or be solvated as individual molecules of L-arginine.

For example, it is believed, and has been observed that L-arginine residues in long or short peptide chains may not accomplish the desired promotion of the desired microbiota within the oral cavity, including with the desired health promoting effect, including the promotion of desired *Veillonella* and *Streptococcus* species as previously discussed.

In some embodiments, the L-arginine may be present as individual molecules present in associated salts and/or acids such as but not limited to, L-arginine HCl (Hydrogen Chloride), and L-arginine glutamate.

In a related embodiment, the at least one amino acid, may be present in the oral microbiota promoting composition at a weight percent level of from about 0.1 wt. % to about 99.9 wt. %, more preferably, from about 5 wt % to about 95 wt %, even more preferably from about 20 wt % to 80 wt %.

In another embodiment, an oral microbiota promoting composition is provided that includes at least one sugar containing substance and at least one amino acid containing substance. The at least one sugar containing substance may include at least one monosaccharide, disaccharide, oligosaccharide, and polysaccharide.

Exemplary monosaccharides may include but are not limited to aldohexoses such as but not limited to mannose including associated isomers, phosphates, salts, acids, and enzymes comprising the same.

Exemplary disaccharides may include but are not limited to disaccharides including at least one of galactose and glucose, such as but not limited to lactose, sucrose, malibiose, maltose, cellobiose and trehalose (also known as mycose or tremalose) including associated isomers, phosphates, salts, acids, and enzymes comprising the same.

Exemplary oligosaccharides may include but are not limited to trisaccharides including at least one or more of galactose, glucose, and fructose, such as but not limited to raffinose (also known as melitose), stachyose, and verbascose, including associated isomers, phosphates, salts, acids, and enzymes comprising the same.

Further, Exemplary polysaccharides may include but are not limited to one or more polysaccharide polymers, such as, but not limited to polysaccharides including malotriose units, including but not limited to pullulan, and fructose polymers, such as, but not limited to inulin and further including associated isomers, phosphates, salts, acids, and enzymes comprising the same.

In a related embodiment, the at least one disaccharide may be present in the oral microbiota promoting composition at a weight percent level of from about 0.1 wt. % to about 99.9 wt. %, more preferably, from about 5 wt % to about 95 wt %, even more preferably from about 20 wt % to 80 wt %.

In a related embodiment, the at least one oligosaccharide may be present in the oral microbiota promoting composition at a weight percent level of from about 0.1 wt. % to about 99.9 wt. %, more preferably, from about 5 wt % to about 95 wt %, even more preferably from about 20 wt % to 80 wt %.

In a related embodiment, the at least one polysaccharide may be present in the oral microbiota promoting composition at a weight percent level of from about 0.1 wt. % to about 99.9 wt. %, more preferably, from about 5 wt % to about 95 wt %, even more preferably from about 20 wt % to 80 wt %.

In another embodiment, the oral microbiota promoting composition may include at least one prebiotic fiber. Exemplary prebiotic fibers may include but are not limited to inulin.

In a related embodiment, the at least one prebiotic fiber may be present in the oral microbiota promoting composition at a weight percent level of from about 0.1 wt. % to about 99.9 wt. %, more preferably, from about 5 wt % to about 95 wt %, even more preferably from about 10 wt % to 30 wt %.

In another embodiment the oral microbiota promoting composition may include additives such as one or more of carbohydrates, amino acids, salts, flavorants, proteins, surfactants, emulsifiers, flavonoids, alcohols, synthetic sweeteners, food preserving agents, and combinations thereof.

In one embodiment, the oral microbiota promoting composition may further include conventional foodstuffs such as one or more of brown sugar, syrup, honey, chocolate, nuts, almonds, spices, cinnamon, and vanilla.

In another embodiment, the oral microbiota promoting composition may further include extract from fruits, such as jujube fruit extract which may include one or more of rhamnose, xylitol, arabitol, fructose, glucose, inositol, sucrose, and maltose.

In a specific exemplary embodiment, an example of making an edible Foodstuff oral microbiota promoting composition is provided below in Example 1:

Example 1

1 cup raffinose
1 cup trehalose
2 tablespoons mannose
1 cup lactose
½ cup maltose
½ cup L-arginine
2 tablespoons pullulan
1 cup inulin
1 cup dark brown sugar
½ cup corn syrup ½ cup honey
1 cup milk chocolate
1 cup chocolate chips
¼ cup toasted almonds (small chips)
¼ tablespoon cinnamon
¼ tablespoon vanilla extract In one embodiment, the above ingredients may be admixed and heated to a temperature sufficient to melt or liquefy, preferably avoiding boiling for an extended period and then poured into a container to cool.

In another embodiment, live bacterium, in accordance with safety requirements or limitations, may be added following cooling (e.g., as a coating). It will be appreciated that adding the bacterium may be limited by applicable safety precautions and may reduce the shelf life of the product.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A method of selectively promoting a desired oral microbiota to treat an inflammation condition caused by an allergic reaction in a subject in need of such treatment comprising:
   providing a preformulated prebiotic edible composition comprising an amino acid containing ingredient comprising L-arginine, the L-arginine configured to be present at a concentration of greater than about 0.1 wt % substantially comprised of separate individual molecules of L-arginine within an oral cavity of the subject;
   substantially removing a biofilm from surfaces comprising the oral cavity, the removing comprising exposing the biofilm to a biofilm degrading enzyme;
   wherein at least one of during and following removal of the biofilm, the composition is contained and at least partially dissolved within an oral cavity of the subject for a period of at least from about 60 seconds to about 3600 seconds on a daily basis comprising at least one day in an effective amount to selectively promote an increased concentration of selected oral microbiota to thereby treat the inflammation condition, the selectively promoted microbiota comprising *Veillonella* and *Streptococcus*.

2. The method of claim 1, wherein the inflammation condition comprises one or more of gingivitis, periodontitis, tonsillitis, rhinosinusitis, pharyngitis, and laryngitis.

3. The method of claim 1, wherein the inflammation condition comprises one or more of lupus, arthritis and autoimmune diseases having the inflammation condition present on one or more of the head, neck and lungs.

4. The method of claim 1, wherein the biofilm degrading enzyme comprises one or more of saccharidases, polysaccharidases, proteases, lipases, polysaccharide lyases, DNases, and glycoproteases.

5. The method of claim 1, wherein the biofilm degrading enzyme comprises one or more hydrolytic enzymes capable of degrading saccharides, polysaccharides, proteins, polypeptides, and lipids.

6. The method of claim 1, wherein the biodegrading enzyme is provided within the oral cavity by at least one of being provided in a carrier and on a support surface.

7. The method of claim 1, wherein the amino acid containing ingredient comprises one or more salts of L-arginine including one or more of L-arginine HCl, and L-arginine glutamate.

8. The method of claim 1, wherein the composition is provided within the oral cavity by at least one of being provided in a carrier and supported on a support surface.

9. The method of claim 1, wherein the composition is provided within the oral cavity from a period of from about 1 consecutive day to about 60 consecutive days.

10. The method of claim 1, wherein removing the biofilm comprises removing a substantial portion of the biofilm from one or more major surface areas within the oral cavity.

11. The method of claim 1, further comprising heating portions of the oral cavity including one or more major surface areas of the oral cavity to a temperature of about 100 deg F. to about 130 deg F.

12. The method of claim 11, wherein heating portions of the oral cavity comprises periodic oral rinsing with a heated liquid.

13. The method of claim 1, wherein removal of the biofilm further comprises at least one of brushing and rubbing the oral cavity.

14. The method of claim 1, wherein the at least one amino acid further comprises at least one of L-cysteine, DL-aspartic acid, L-glutamic acid, L-serine, and L-tyrosine.

15. The method of claim 1, wherein the amino acid is present in the composition at a weight percent level of from greater than about 0.1 wt. % to about 99.9 wt. %.

16. The method of claim 1, wherein the composition further comprises a sugar, the sugar comprising one or more monosaccharides, disaccharides, oligosaccharides, and polysaccharides.

17. The method of claim 16, wherein the sugar comprises one or more of mannose, lactose, malibiose, maltose, cellobiose, trehalose, raffinose, stachyose, and verbascose.

18. The method of claim 16, wherein the composition further comprises polysaccharide polymers.

19. The method of claim 18, wherein the polysaccharide polymers comprise one or more of pullulan and inulin.

20. The method of claim 16, wherein the sugar comprises at least one of jujube fruit extract and one or more of rhamnose, xylitol, arabitol, fructose, glucose, inositol, sucrose, and maltose.

21. The method of claim 16, wherein the sugar is present in the composition at a weight percent level of from about 0.1 wt. % to about 95 wt. %.

22. The method of claim 1, wherein at least one of the composition and oral cavity further comprises live bacteria comprising a lactic acid producing bacterium and a lactate fermenting bacterium at a level of from about 1000 to about 1,000,000,000 living cells.

23. The method of claim 1, wherein *Streptococcus* includes one or more of *S. salivarius* and *S. thermophilus* and wherein *Veillonella* comprises one or more of *V. dispar* and *V. parvula*.

24. The method of claim 1, wherein the selected microbiota comprising *Veillonella* and *Streptococcus* are selectively promoted to the increased concentration of about 40 percent to about 70 percent with respect to all bacterial species present from a sampled surface comprising the oral cavity.

25. A method of selectively promoting a desired oral microbiota to treat an inflammation condition caused by an allergic reaction in a subject in need of such treatment comprising:
   providing a preformulated prebiotic edible composition comprising an amino acid containing ingredient comprising L-arginine, the L-arginine configured to be present at a concentration of greater than about 0.1 wt % substantially comprised of separate individual molecules of L-arginine within an oral cavity of the subject;
substantially removing a biofilm from surfaces comprising the oral cavity, the removing comprising exposing the biofilm to a biofilm degrading enzyme;
wherein following removal of the biofilm, the composition is contained and at least partially dissolved within an oral cavity of the subject for a period of at least from about 60 seconds to about an 3600 seconds on a daily basis comprising at least one day in an effective amount to selectively promote an increased concentration of selected oral microbiota to thereby treat the inflammation condition, the selectively promoted microbiota comprising *Veillonella* and *Streptococcus* at a concentration of about 40 percent to about 70 percent with respect to all bacterial species present from a sampled surface comprising the oral cavity.

\* \* \* \* \*